US012758217B2

(12) United States Patent
Nie et al.

(10) Patent No.: US 12,758,217 B2
(45) Date of Patent: Oct. 13, 2026

(54) SURGICAL INSTRUMENT HAVING BENDABLE ACTUATOR

(71) Applicants: YISI (SUZHOU) MEDICAL TECHNOLOGY CO., LTD., Jiangsu (CN); EZISURG MEDICAL CO., LTD., Shanghai (CN)

(72) Inventors: Honglin Nie, Shanghai (CN); Guang Yang, Shanghai (CN); Xiliang Zhang, Shanghai (CN); Yang Jiang, Shanghai (CN); Xiufeng Shi, Shanghai (CN); Anhua Li, Shanghai (CN)

(73) Assignees: YISI (SUZHOU) MEDICAL TECHNOLOGY CO., LTD., Jiangsu (CN); EZISURG MEDICAL CO., LTD., Shanghai (CN)

( * ) Notice: Subject to any disclaimer, the term of this patent is extended or adjusted under 35 U.S.C. 154(b) by 0 days.

(21) Appl. No.: 15/768,608

(22) PCT Filed: Jun. 29, 2016

(86) PCT No.: PCT/CN2016/087641
§ 371 (c)(1),
(2) Date: Apr. 16, 2018

(87) PCT Pub. No.: WO2017/063382
PCT Pub. Date: Apr. 20, 2017

(65) Prior Publication Data
US 2018/0289372 A1 Oct. 11, 2018

(30) Foreign Application Priority Data
Oct. 16, 2015 (CN) ......................... 201510672007.2

(51) Int. Cl.
*A61B 17/072* (2006.01)
*A61B 17/295* (2006.01)
(Continued)

(52) U.S. Cl.
CPC ...... *A61B 17/07207* (2013.01); *A61B 17/295* (2013.01); *A61B 2017/0046* (2013.01);
(Continued)

(58) Field of Classification Search
CPC .... A61B 2017/2927; A61B 2017/0046; A61B 17/07207; A61B 17/295;
(Continued)

(56) References Cited

U.S. PATENT DOCUMENTS 5,405,344 A 4/1995 Williamson et al.
5,702,408 A * 12/1997 Wales .............. A61B 17/07207 606/205
(Continued)

FOREIGN PATENT DOCUMENTS

CN 1720868 A 1/2006
CN 1993083 A 7/2007
(Continued)

OTHER PUBLICATIONS

International Search Report and Written Opinion mailed Sep. 21, 2016 in International Application PCT/CN2016/087641.
(Continued)

*Primary Examiner* — Andrew M Tecco
(74) *Attorney, Agent, or Firm* — Fox Rothschild LLP

(57) ABSTRACT

A surgical instrument comprises an actuator, an extension tube and a controller, wherein the near end of the extension tube is connected with the controller, the far end of the extension tube is connected with the actuator, and the actuator can rotate relative to the far end of the extension tube. The controller comprises a bend control mechanism capable of moving in at least one direction. The extension tube comprises a first flexible component and moves in at least one direction through the bend control mechanism. The first flexible component enables the actuator to rotate rela-
(Continued)

tive to the far end of the extension tube towards at least one side. A bendable magazine is further provided. The actuator can bend relative to the far end of the extension tube by a larger angle through the flexible components, thereby being suitable for medical treatment under more complex clinical conditions.

7 Claims, 6 Drawing Sheets

(51) Int. Cl.
*A61B 17/00* (2006.01)
*A61B 17/29* (2006.01)

(52) U.S. Cl.
CPC ............... *A61B 2017/00818* (2013.01); *A61B 2017/07257* (2013.01); *A61B 2017/07271* (2013.01); *A61B 2017/07285* (2013.01); *A61B 2017/2927* (2013.01)

(58) Field of Classification Search
CPC A61B 2017/00818; A61B 2017/07257; A61B 2017/07271; A61B 2017/2943
USPC ............................................ 227/175.1–182.1
See application file for complete search history.

(56) References Cited

U.S. PATENT DOCUMENTS 5,704,534 A * 1/1998 Huitema .......... A61B 17/07207 227/176.1
5,865,361 A 2/1999 Milliman et al.
7,703,653 B2 4/2010 Shah et al.
9,492,146 B2 11/2016 Kostrzewski et al.
10,245,029 B2 * 4/2019 Hunter ............. A61B 17/07207
10,368,861 B2 * 8/2019 Baxter, III ........... A61B 17/068
10,405,863 B2 * 9/2019 Wise .................... A61B 17/068
11,903,580 B2 * 2/2024 Shelton, IV ......... A61B 17/068
2005/0251175 A1 11/2005 Weisenburgh et al.
2005/0277955 A1 12/2005 Palmer et al.
2008/0188871 A1 8/2008 Smith et al.
2010/0163597 A1 * 7/2010 Shah ................ A61B 17/07207 227/175.1
2011/0240712 A1 * 10/2011 Kostrzewski .... A61B 17/07207 227/176.1
2012/0080475 A1 4/2012 Smith et al.
2012/0310220 A1 12/2012 Malkowski et al.
2012/0323263 A1 12/2012 McClurg et al.
2013/0126586 A1 5/2013 Zhang et al.
2013/0255804 A1 10/2013 Smith et al.
2013/0274722 A1 * 10/2013 Kostrzewski .... A61B 17/00234 606/1
2014/0243801 A1 * 8/2014 Fanelli ............. A61B 17/07207 606/1
2014/0303668 A1 10/2014 Nicholas et al.
2016/0030043 A1 2/2016 Fanelli et al.
2016/0174970 A1 * 6/2016 Shelton, IV ......... A61B 17/068 227/180.1
2016/0367256 A1 * 12/2016 Hensel ................. A61B 17/068

FOREIGN PATENT DOCUMENTS

CN 101594816 A 12/2009
CN 102469997 A 5/2012
CN 103181808 A 7/2013
CN 105434002 A 3/2016
CN 205339036 U 6/2016
EP 0717959 A2 6/1996
JP 2001-517473 A 10/2001
JP 2013-146604 A 8/2013
JP 2013-255804 A 12/2013
JP 2016-508413 A 3/2016

OTHER PUBLICATIONS

Search Report issued Jul. 9, 2017 in Chinese Application 201510672007.2.
Office Action issued Jul. 17, 2017 in Chinese Application 201510672007.2.
Notification to Grant Patent Right for Invention issued Sep. 12, 2017 in Chinese Application 201510672007.2.
Office Action issued Dec. 17, 2017 in Japanese Application 2018-538925.
International Preliminary Report on Patentability issued Apr. 17, 2018 in International Application PCT/CN2016/087641.
Search Report issued Feb. 22, 2019 in Japanese Application 2018-538925.
Office Action issued Feb. 26, 2019 Japanese Application 2018-538925.
Extended European Search Report issued May 29, 2019 in European Application 16854766.9.
Office Action issued Nov. 1, 2019 in Russian Application 2018117902/14.
Office Action issued Jun. 16, 2020 in Brazilian Application BR112018007509.

* cited by examiner

SURGICAL INSTRUMENT HAVING BENDABLE ACTUATOR

CROSS-REFERENCE TO RELATED APPLICATION

The present application claim priority to International Patent Application No. PCT/CN2016/087641, filed on Jun. 29, 2016, which claims priority to Chinese Patent Application 201510672007.2 filed Oct. 16, 2015, the disclosure of which are incorporated herein by reference in their entireties.

BACKGROUND OF THE INVENTION

Technical Field

The invention relates to a medical instrument, in particular to an endoscope instrument.

Description of Related Art

A surgical stapler is a surgical instrument. According to the action principle of the surgical stapler, two corresponding actuators (generally comprising a anvil assembly and a cartridge assembly) are closed to clamp tissue, and metal suturing staples in the cartridge of the stapler are then pushed out to suture tissue. Certain staplers are further provided with a cutter used for incising sutured tissue.

With the advance in technology, traditional surgery methods are gradually replaced by endoscope surgery. As for the endoscope surgery, a plurality of small incisions with the diameter of 5-12 mm are punctured at different positions of the abdomen or the chest, a camera lens and various special surgical instruments are inserted into the abdomen cavity through these incisions, images, taken by the camera inserted into the abdomen cavity, of various visceral organs in the abdomen cavity are transmitted to a video screen to be observed by a surgeon, and the surgery is completed through extracorporeal operation by means of various surgical instruments. An endoscope stapler plays a key role in the surgery.

However, endoscope surgery also has limitations. As the space in the abdomen cavity or the thoracic cavity is limited, traditional linear endoscope staplers cannot effectively reach the surgical site to clamp, transect and staple tissue under certain extreme conditions, and thus endoscope staplers provided with bendable actuators are created.

The Endo GIA Universal stapler and magazine of American Tyco Healthcare Company (later renamed as Covidien) are typical products with the above function. The product of the patent application No. US2010/0237131A1 to America adopts a hinge-eccentric rigid connecting rod hinge structure to achieve deflection of an actuator. Limited by the structural design principle, the maximum bending angle of the actuator of the magazine is only 45°. In the surgery requiring an actuator to bend by a large angle, focuses on certain parts cannot be removed through the actuator capable of bending by a small angle. For instance, in low rectal rectectomy, as the entry angle of an instrument is limited by the space of the pelvic cavity, although the actuator of the magazine bends, the actuator still cannot suture or dissect tissue perpendicular to the rectum in part of surgery, and consequentially, patents with tumors at low positions cannot be treated through the instrument.

Thus, in this field, a surgical instrument provided with an actuator capable of bending by a larger angle is needed to adapt to medical treatment under more complex clinic conditions.

BRIEF SUMMARY OF THE INVENTION

For this reason, the invention aims to provide a surgical instrument. The surgical instrument comprises an actuator, an extension tube and a controller, wherein the near end of the extension tube is connected with the controller, the far end of the extension tube is connected with the actuator, and the actuator is capable of rotating relative to the far end of the extension tube; the controller comprises a bend control mechanism capable of moving in at least one direction; and the extension tube comprises a first flexible component and moves in at least one direction through the bend control mechanism, and the first flexible component enables the actuator to rotate towards at least one side relative to the far end of the extension tube.

According to one aspect, the extension tube further comprises a second flexible component, and the far end of the first flexible component and the far end of the second flexible component are respectively connected to the two sides of the central axis of the actuator. When moving in a first direction, the bend control mechanism drives the first flexible component to move towards the near end of the bend control mechanism and drives the second flexible component to move towards the far end of the bend control mechanism, and then the actuator is driven to rotate towards a first side relative to the far end of the extension tube. When moving in a second direction, the bend control mechanism drives the first flexible component to move towards the far end of the bend control mechanism and drives the second flexible component to move towards the near end of the bend control mechanism, and then the actuator is driven to rotate toward a second side relative to the far end of the extension tube.

According to one aspect, the bend control mechanism comprises a gear, a first rack and a second rack. The gear is engaged with the first rack and the second rack. The first rack is connected with the near end of the first flexible component, and the second rack is connected with the near end of the second flexible component.

According to one aspect, the extension tube further comprises a magazine sleeve, magazine inner tubes, a bend control rod, a gear, a first rack and a second rack, wherein the magazine inner tubes and the magazine sleeve are arranged coaxially; the gear is rotatably arranged on the magazine inner tubes, the first rack and the second rack are arranged on the two sides of the gear, and the gear is engaged with the first rack and the second rack; and the bend control rod is arranged in the magazine sleeve, the near end of the bend control rod is connected with the bend control mechanism, the far end of the bend control rod is fixedly connected with the first rack, the first rack is further fixedly connected with the near end of the first flexible component, and the second rack is fixedly connected with the near end of the second flexible component. The bend control mechanism controls movement of the bend control rod: when moving towards the near end of the bend control mechanism, the bend control rod pulls the first rack and then pulls the first flexible component, and the actuator is pulled by the first flexible pulling sheet to rotate towards a first side relative to the far end of the extension tube; and when moving towards the far end of the bend control mechanism, the bend control rod pushes the first rack and then drives the second rack to move towards the near end through the gear so as to pull the second flexible component, and the actuator is pulled by the second flexible pulling sheet to rotate towards a second side relative to the far end of the extension tube.

According to one aspect, the magazine inner tubes include a first magazine inner tube and a second magazine inner tube, the first magazine inner tube and the second magazine inner tube are coaxial with the magazine sleeve, and the gear is rotatably arranged on the first magazine inner tube or the second magazine inner tube.

According to one aspect, the actuator comprises an anvil assembly and a cartridge assembly, wherein the cartridge assembly comprises a cartridge, one or more suturing staples, one or more staple pushing blocks, and a cartridge holder. The surgical instrument further comprises a driving assembly. The driving assembly comprises a cutter and a flexible cutter bar. The near end of the anvil assembly is movably connected with the near end of the cartridge holder. The driving assembly drives the actuator to switch to in a first state or a second state.

According to one aspect, the rotation angle of the actuator towards at least one side relative to the far end of the extension tube is any numerical value from 0° to 180°.

According to one aspect, the far end of the extension tube is connected with the actuator through one or more hinges, the first flexible pulling sheet does not pass through the center of the hinge so that at least one flexible pulling sheet can provide rotation torque for the actuator with the hinge as the rotation axis, and the actuator is driven to rotate towards at least one side relative to the far end of the extension tube.

The invention further provides a bendable magazine. The bendable magazine comprises a magazine body, an intermediate connecting part and an actuator connected with the magazine body through the intermediate connecting part, wherein the magazine body comprises a bend control mechanism and at least one flexible component; and the bend control mechanism is capable of moving in at least one direction, and then at least one flexible component enables the actuator to rotate towards at least one side relative to the magazine body.

According to one aspect, the magazine is applicable to an endoscope stapler.

According to one aspect, the magazine further comprises a second flexible component, and the far end of the first flexible component and the far end of the second flexible component are respectively connected to the two sides of the central axis of the actuator. When moving in a first direction, the bend control mechanism drives the first flexible component to move towards the near end of the bend control mechanism and drives the second flexible component to move towards the far end of the bend control mechanism, and then the actuator is driven to rotate towards a first side relative to the far end of the magazine body; and when moving in a second direction, the bend control mechanism drives the first flexible component to move towards the far end of the bend control mechanism and drives the second flexible component to move towards the near end of the bend control mechanism, and then the actuator is driven to rotate toward a second side relative to the far end of the magazine body.

According to one aspect, the bend control mechanism of the magazine comprises a gear, a first rack and a second rack. The gear is engaged with the first rack and the second rack. The first rack is connected with the near end of the first flexible component, and the second rack is connected with the near end of the second flexible component.

According to one aspect, the magazine body further comprises a magazine sleeve, magazine inner tubes, a bend control rod, a gear, a first rack and a second rack, wherein the magazine inner tubes and the magazine sleeve are arranged coaxially, the gear is rotatably arranged on the magazine inner tubes, the first rack and the second rack are arranged on the two sides of the gear, and the gear is engaged with the first rack and the second rack; the bend control rod is arranged in the magazine sleeve, the near end of the bend control rod is connected with the bend control mechanism, the far end of the bend control rod is fixedly connected with the first rack, the first rack is further fixedly connected with the near end of the first flexible component, and the second rack is further fixedly connected with the near end of the second flexible component. The bend control mechanism controls movement of the bend control rod: when moving towards the near end of the bend control mechanism, the bend control rod pulls the first rack and then pulls the first flexible component, and the actuator is pulled by the first flexible pulling sheet to rotate towards a first side relative to the far end of the magazine body; and when moving towards the far end of the bend control mechanism, the bend control rod pushes the first rack and then drives the second rack to move towards the near end through the gear so as to pull the second flexible component, and the actuator is pulled by the second flexible pulling sheet to rotate toward a second side relative to the far end of the magazine body.

According to one aspect, the magazine inner tubes include a first magazine inner tube and a second magazine inner tube. The first magazine inner tube and the second magazine inner tube are coaxial with the magazine sleeve. The gear is rotatably arranged on the first magazine inner tube or the second magazine inner tube.

According to one aspect, the rotation angle of the actuator towards at least one side relative to the far end of the magazine body is any numerical value from 0° to 180°.

According to the surgical instrument of the invention, the flexible components are adopted to enable the actuator to bend relative to the far end of the extension tube, and thus the actuator is capable of bending by a larger angle to adapt to medical treatment under more complex clinic conditions. For instance, surgery can be performed on parts with limited spaces (such as the thoracic cavity and the pelvic cavity) more conveniently, and thus the problems which cannot be solved by other surgical instruments are solved. The surgical instrument provided with the actuator capable of bending by a large angle of the invention can achieve focus excision, tissue incision and suturing at various inaccessible positions and thus is beneficial to more patients. For instance, for patient suffering from rectal cancer, the actuator of the surgical instrument is still capable of rotating to be perpendicular to the rectum when located at the lowermost position of the rectum, and thus more patients suffering from low rectal cancer can receive minimally invasive surgery.

Furthermore, the surgical instrument of the invention not only can be applied to surgery, but also can be applied to relevant treatment and diagnosis.

Furthermore, invention not only can be applied to endoscope staplers, but also can be applied to closers, electric scalpels and other products.

BRIEF DESCRIPTION OF THE SEVERAL VIEWS OF THE DRAWINGS

Drawings comprised in and constituting one part of the description show illustrative embodiments of the invention and are used for explaining the characteristics of the invention together with the summery of the invention mentioned above and the detailed description of the invention mentioned below.

DETAILED DESCRIPTION OF THE INVENTION

Figure 1:
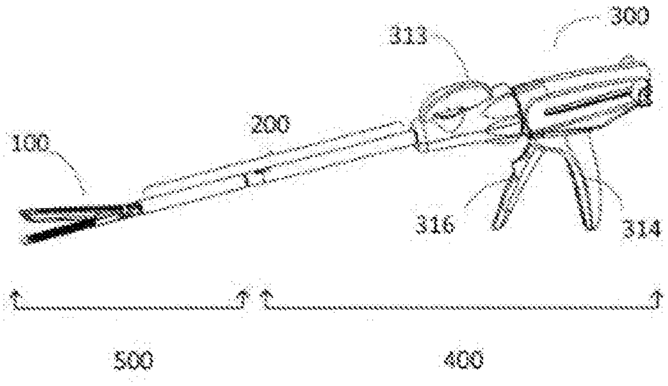
FIG. 1 is a design diagram of a surgical instrument in one embodiment of the invention.

Various embodiments are described m detail with the accompanying drawings. If possible, identical reference signs are used for indicating identical or similar parts in the drawings. Specific embodiments and effects realized are used only for illustration and do not limit the scope of the invention or the claims.

The expression 'illustrative' in the description refers to 'being used as demonstrations or examples or for illustration'. Any 'illustrative' realization in the description is not definitely interpreted as being superior to or better than other realizations.

For a brief description, the instrument of the invention is explained with a stapler as an example. Those skilled in the field understand that the surgical instrument provided with the bendable actuator of the invention is not limited to endoscope staplers. The technique of the invention can also be applied to other products such as closers and electric scalpels.

FIG. 1 is a design diagram of a surgical instrument in one embodiment of the invention. As is shown in FIG. 1, the surgical instrument comprises an actuator 100, an extension tube 200 and a controller 300. The extension tube 200 is movably connected with the far end of the controller 300 and connected with the near end of the actuator 100. The extension tube 200 forms a connecting passage and is used for transmitting the motion of the controller 300 to the actuator 100. The controller 300 is used for controlling operation of the instrument.

The surgical instrument of the invention can adopt an integrated design, namely, as a whole, the extension tube 200 is connected with the far end of the controller 300 and the near end of the actuator 100. The length of the extension tube 200 can be changed according to different indications and specific conditions of patients.

As is shown in FIG. 1, the surgical instrument of the invention can also adopt a separated design. In the embodiment shown by FIG. 1, the surgical instrument adopting the separated design can comprise a stapler 400 and a magazine 500. In use, the stapler 400 and the magazine 500 can be assembled into a whole in a certain assembly manner. In the separated design, one stapler can be matched with various types of magazines in surgery.

Figure 3:
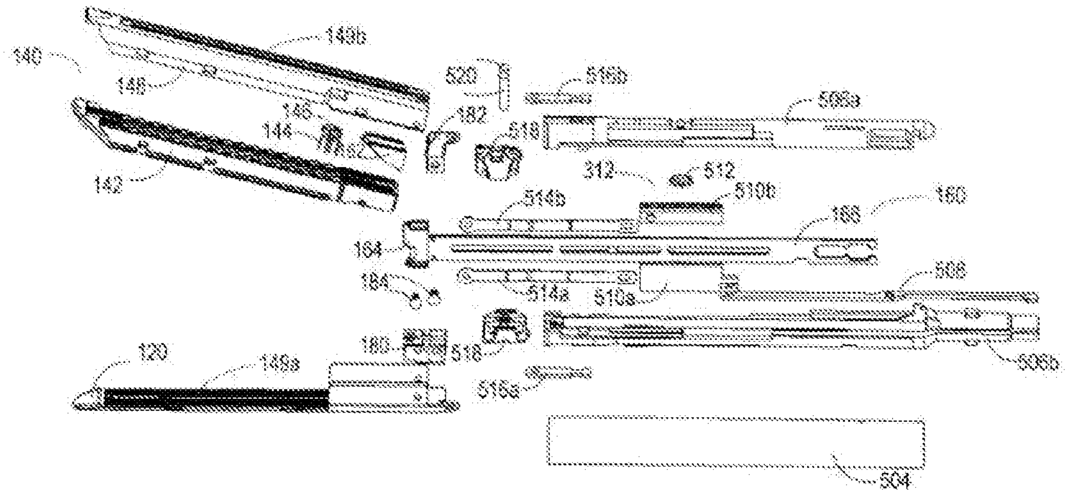
FIG. 3 is an exploded view of a magazine in a surgical instrument in one embodiment of the invention.

As is shown in FIG. 1 and FIG. 3, the controller 300 can comprise a bend control mechanism 312. For instance, the bend control mechanism 312 can move in a first direction and in a second direction. As an example, the bend control mechanism 312 can be a gear reversing mechanism. The bend control mechanism 312 can comprise a gear 512, a first rack 510*a* and a second rack 510*b*. It is understandable that the gear 512, the first rack 510*a* and the second rack 510*b* can also be disposed in the extension tube. A handle component can be used as the controller 300. In this case, the controller 300 can further comprise a bend control spanner 313, a fixed handle 314, a movable handle 316 (such as a percussion trigger) oppositely and movably connected with the fixed handle, and a transmission mechanism capable of transmitting the motion of the movable handle 316 to the actuator. For instance, in operation, the bend control spanner 313 can be rotated to control the actuator 100 to rotate by a certain angle at the far end of the extension tube 200 and on the plane perpendicular to the hinge rotation axis. Every time the bend control spanner rotates to a specific position, the actuator 100 correspondingly rotates by a certain specific angle. The actuator 100 can rotate by different angles to adapt to different clinical applications. The percussion trigger is pulled, and then the actuator can continuously clamp, suture and cut human tissue. The function of rotating the bend control spanner to rotate the actuator and the function of operating the percussion trigger to drive the actuator to work are mutually independent. Generally, the operating process of the surgical instrument of the invention is as follows: the bend control spanner is operated first to control the actuator to rotate to an angle suitable for a clinical application, the position of tissue in the jaw of the actuator is then adjusted, and afterwards, the percussion trigger is operated to achieve tissue clamping, suturing and incision.

A detailed description is given as follows with the endoscope stapler adopting the separated design as an example.

Figure 2:
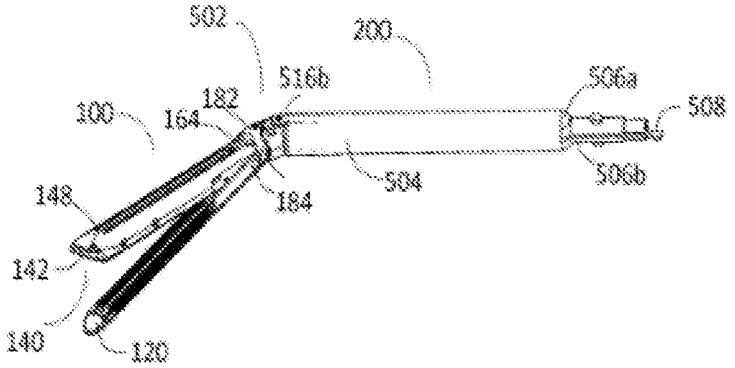
FIG. 2 is an overall diagram of a magazine in a surgical instrument in one embodiment of the invention.

FIG. 2 and FIG. 3 respectively show the overall diagram and the exploded view of the magazine in the surgical instrument in one embodiment of the invention.

In one embodiment of the invention, a bendable magazine 500 is provided. As an example, the magazine 500 can comprise a magazine body 501, an intermediate connecting part 502, an actuator 100 and a driving assembly 160.

As an example, the magazine body 501 can mainly comprise a magazine sleeve 504, a first magazine inner tube 506*a*, a second magazine inner tube 506*b*, a bend control rod 508, a first rack 510*a*, a second rack 510*b*, a gear 512, a first flexible pulling sheet 514*a*, a second flexible pulling sheet 514*b*, a first connecting sheet 516*a*, a second connecting sheet 516*b*, and the like. In the embodiment, the first magazine inner tube 506*a*, the second magazine inner tube 506*b* and the magazine sleeve 504 are arranged coaxially. The gear 512 is rotatably arranged on the first magazine inner tube 506*a* or the second magazine inner tube 506*b*. Although the FIGs show that multiple magazine inner tubes such as the first magazine inner tube 506*a* and the second magazine inner tube 506*b* are adopted, it is understandable that in certain other embodiments, an integrated magazine inner tube is also available.

The intermediate connecting part 502 can comprise intermediate connectors 518 (two intermediate connectors are shown in FIG. 3) and a rivet b 520.

The actuator 100 can comprise an anvil assembly 120 and a cartridge assembly 140 and can further comprise an anvil connector 180, a gland 182 and a rivet a 184. The anvil assembly 120 can comprise a staple forming face with a plurality of rows of staple forming slots. The cartridge assembly 140 can comprise a cartridge 142, one or more suturing staples 144, one or more staple pushing blocks 146 and a cartridge holder 148. The upper surface of the cartridge 142 is a tissue contact surface, and the cartridge 142 is mounted in the cartridge holder 148. The near end of the anvil assembly 120 is movably connected with the near end of the cartridge holder 148 of the cartridge assembly 140, and the anvil assembly 120 can be switched to be in an open state or a closed state. The driving assembly 160 is connected with the transmission mechanism and used for, for instance, converting the motion of the percussion trigger into the closing, percussion or opening motion of the actuator 100. Generally, the anvil assembly 120 and the cartridge holder 148 can respectively comprise a longitudinal groove 149*a* and a longitudinal groove 149*b*, and the longitudinal grooves 149*a*, 149*b* allow the driving assembly 160 to pass through. When the driving assembly 160 moves towards the far end of the actuator 100 through the longitudinal groove 149*a* or the longitudinal groove 149*b*, the anvil assembly 120 and the cartridge assembly 140 can be driven to switch to a second state (for instance, the closed state) from a first state (for instance, the open state), a staple pushing slider 162 and the staple pushing block 146 are driven to eject the suturing staple 144 out, the suturing staple 144 is then formed in one staple forming slot in the staple forming surface of the anvil assembly 120, and vice versa. Thus, the actuator is driven by the driving assembly to switch to the first state or the second state.

Generally, the driving assembly 160 can comprise a slider 162, a cutter 164 and a flexible cutter bar 166. The cutter 164 is used for incising tissue between a plurality of rows of staple lines after the tissue is sutured by the suturing staple 144.

The magazine body 501, the intermediate connector 518 and the actuator 100 can be connected through one or more rotary hinges such as a hinge 552*a* and a hinge 552*b*. As an example, the two hinges 552*a*, 552*b* are spatially in parallel and perpendicular to the bendable plane of the actuator.

According to one example of the invention, the first magazine inner tube 506*a* and the second magazine inner tube 506*b* are coaxial with the magazine sleeve 504. The bend control rod 508 is arranged between the first magazine inner tube 506*a* and the second magazine inner tube 506*b* and fixedly connected with the first rack 510*a*. The first rack 510*a* and the second rack 510*b* are respectively arranged on the two sides of the first magazine inner tube 506*a* and are in engaged transmission through the gear 512 disposed on the rotation axis of the first magazine inner tube 506*a*. The first rack 510*a* is fixedly connected with the near end of the first flexible pulling sheet 514*a*. The second rack 510*b* is fixedly connected with the near end of the second flexible pulling sheet 514*b*. The first flexible pulling sheet 514*a* and the second flexible pulling sheet 514*b* penetrate through the intermediate connector 518 to be respectively connected to the left side and the right side of the central axis of the actuator 100.

According to one example of the invention, the flexible cutter bar 166 of the driving assembly 160 is arranged inside the magazine body 501 and penetrates through the intermediate connector 518. The cutter 164 and the slider 162 are arranged in the actuator 100.

When the magazine 500 is mounted on the stapler 400, the bend control rod 508 on the magazine 500 can be controlled to advance or retreat through the bend control mechanism 312 on the stapler 400.

Figure 4:
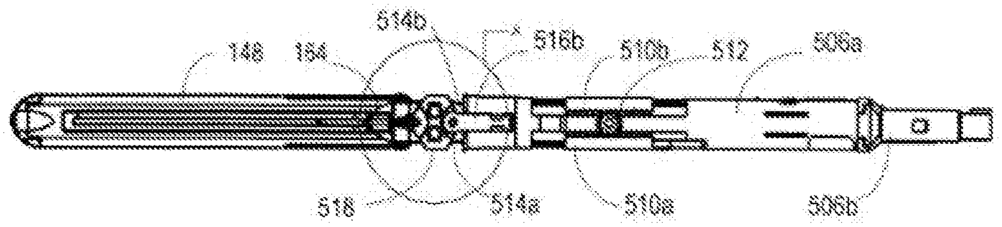
FIG. 4 is a diagram of an actuator, in a linear state, of a magazine in a surgical instrument in one embodiment of the invention.
Figure 5:
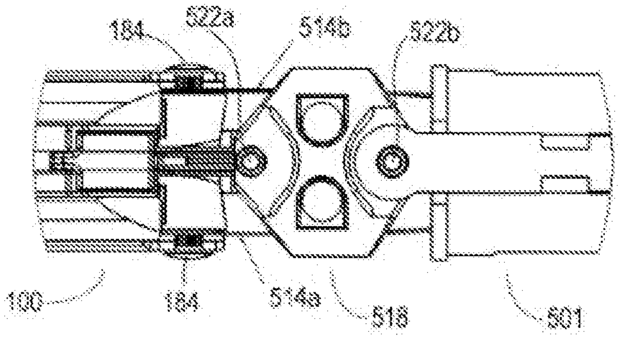
FIG. 5 is a local view of FIG. 4.

FIG. 4 and FIG. 5 respectively show a diagram and a local view A of the actuator, in a linear state, of the magazine in the surgical instrument in one embodiment of the invention.

As is shown in FIG. 4, according to one embodiment of the invention, the central axis of the actuator 100 is collinear with the central axis of the connecting mechanism (such as the magazine body or the extension tube). In this embodiment, the two flexible pulling sheets 514*a*, 514*b* are fixedly mounted on the rivet a 184 of the actuator 100. Through the design, the joints of the flexible pulling sheets 514*a*, 514*b* and the actuator deviate from the central symmetry plane where the rotation axes of the two hinges 522*a*, 522*b* are located, and the flexible pulling sheets 514*a*, 514*b* do not pass through the center of the hinges. Thus, with the hinges as the rotation axes, the flexible pulling sheets provide certain rotation torque for the actuator to drive the actuator to rotate.

Figure 6:
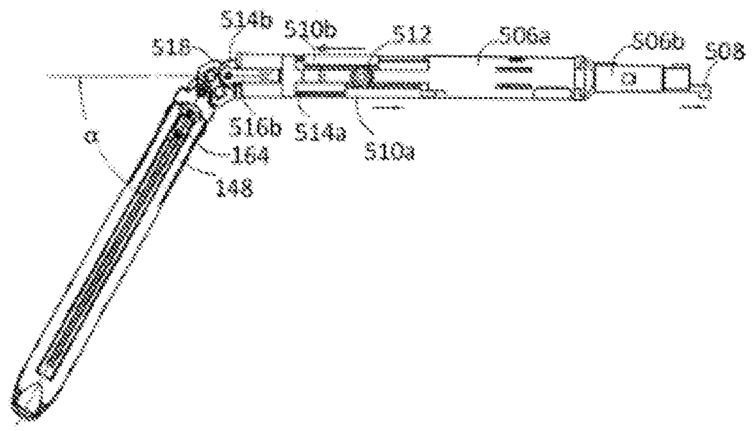
FIG. 6 is a diagram of an actuator, bending towards a first side, of a magazine in a surgical instrument in one embodiment of the invention
Figure 7:
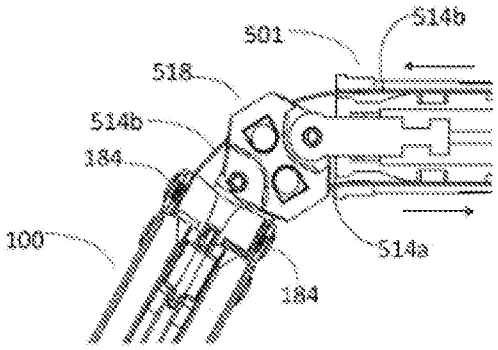
FIG. 7 is a local view of FIG. 6.

FIG. 6 and FIG. 7 respectively show a diagram and a local view of the actuator, bending towards a first side, of the magazine in the surgical instrument in one embodiment of the invention.

As is shown in the FIGs, when pulled, the bend control rod 508 pulls the first rack 510*a* to move towards the near end of the magazine 500 (as indicated by the arrow), and then the first rack 510*a* pulls the first flexible pulling sheet 514*a*. At the moment, the first rack 510*a* drives the gear 512 to rotate, the second rack 510*b* is then driven to move towards the far end of the magazine 500 (as indicated by the arrow), and the second flexible pulling sheet 514*b* is released. In this way, the actuator 100 of the magazine is bent toward the first side (for instance, in the anticlockwise direction shown in the FIGs). The rotation angle of the actuator 100 relative to the magazine body 501 is a. By controlling the feed amount of the bend control rod 508 through the bend control mechanism 312 on the stapler 400, the rotation angle $\alpha$ of the actuator 100 can be controlled. According to one embodiment of the invention, a can be any numerical value from 0° to 180° (such as 0°, 30°, 45°, 60°, 90°, 120°, 135° and 180°).

As can be seen from the FIGs, the first flexible pulling sheet is tensioned, the second flexible pulling sheet is released, and thus the actuator is driven to bend. In this embodiment, the gear is engaged with the two racks, and the two racks move in opposite directions, so that when the actuator rotates, the displacement generated by the first tensioned flexible pulling sheet and the displacement generated by the second released flexible pulling sheet are equal and thus counteracted. In the design of the invention, the opposite displacements of the two flexible pulling sheets can also be counteracted through other methods.

Figure 8:
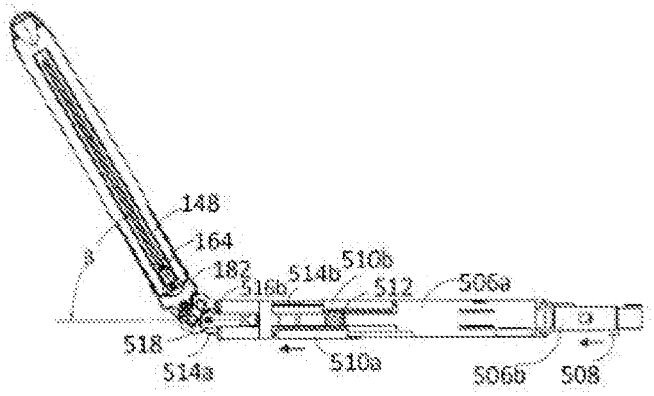
FIG. 8 is a diagram of an actuator, bending towards a second side, of a magazine in a surgical instrument in one embodiment of the invention.

FIG. 8 shows a diagram of the actuator, bending towards a second side, of the magazine in the surgical instrument in one embodiment of the invention.

As is shown in the FIG, when pushed, the bend control rod 508 pushes the first rack 510 to move towards the far end of the magazine 500 (as indicated by the arrow), and the first flexible pulling sheet 514*a* is released. The first rack 510*a* drives the gear 512 to rotate, the second rack 510*b* is then driven to move towards the near end of the magazine 500 (as indicated by the arrow), the second rack 510*b* pulls the second flexible pulling sheet 514*b* to make the actuator 100 of the magazine bend towards the second side (for instance, in the clockwise direction shown in the FIG), and the rotation angle is p. By controlling the feed amount of the bend control rod 508 through the bend control mechanism 312 on the stapler 400, the rotation angle p of the actuator can be controlled. According to one embodiment of the invention, p can be any numerical value from 0° to 180° (such as 0°, 30°, 45°, 60°, 90°, 120°, 135° and 180°).

The principle for the actuator to bend towards the second side is similar to the principle for the actuator to bend towards the first side and is different in that the second flexible pulling sheet is tensioned and the first flexible pulling sheet is released.

Figure 9:
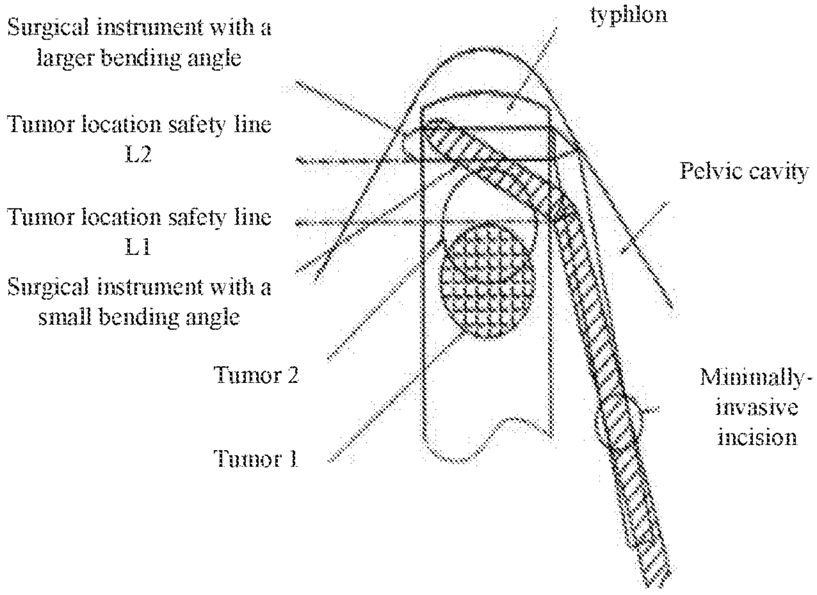
FIG. 9 is a usage diagram of a surgical instrument in one embodiment of the invention.

FIG. 9 shows a usage diagram of the surgical instrument in one embodiment of the invention.

The surgical instrument of the invention can be applied to pulmonary surgery and digestive tract (comprising stomach and intestine) surgery. The pulmonary surgery is generally for focus excision. As for the digestive tract surgery, intestinal canals generally need to be reconnected after focus excision.

Generally, the actuator of the magazine of the bendable endoscope stapler can bend, the near end of the actuator is connected with the bend control mechanism in the controller (such as a stapler handle) through an intermediate mechanism (such as the bend control rod 508 in the FIGs), and the bend control mechanism can be adjusted to control the actuator to bend by multiple angles. In the initial state, the central axis of the actuator is collinear with the central axis of the connecting mechanism, the actuator of the stapler stretches into the pleural cavity or the abdominal cavity through a trocar, the actuator is controlled to bend by a certain angle through extracorporeal control over the bend control mechanism on the handle, and a series of operations such as clamping, transecting and suturing are performed on the surgical site. After the surgery is completed, the actuator is controlled to be in the linear state again through extracorporeal control over the bend control mechanism on the handle and then is pulled out of the body.

For instance, as for the digestive tract surgery, to completely remove a tumor and prevent tumor tissue residues in clinic, the transection line is generally about 5 cm away from the boundary of the tumor. When a rectal cancer tumor is close to the lower portion of the anus of the patient, the actuator of the stapler needs to stretch to a lower position in the narrow pelvic cavity; however, as the entry position of the stapler is limited by the hip bone, of actuator of a stapler with a small bending angle cannot perpendicularly transect the rectum, and consequentially, the surgical risk of incomplete tumor excision is increased.

As can be seen from the FIG, a surgical instrument (with a section line) comprising an actuator with a small bending angle cannot perpendicularly transect the rectum, but a stapler (without a section line) comprising an actuator with a large bending angle can perpendicularly transect the rectum Moreover, a surgical instrument comprising an actuator with a larger bending angle can transect a tumor (tumor 2) at a lower position. When the rotation angle of the actuator of the surgical instrument is further increased, a tumor at a lower position can be incised, and thus the surgical instrument can be well applied to low rectal cancer surgery or other conditions with the in-vivo space limited.

According to the surgical instrument of the invention, the rotation angle of the actuator can reach 90° or even 180° to adapt to extreme applications.

According to another embodiment of the invention, the flexible pulling sheets 512*a*, 512*b* can be replaced with wire ropes, such as single-strand wires, multi-strand intertwined wires or other flexible components. It should be understood that the flexible pulling sheets and the wire ropes are only for illustrative description and are not used for limiting the invention, and those skilled in the field can think out more other similar flexible components to realize bending of the actuator. These realization modes are also within the scope of the invention.

In addition, it also should be understood that all the embodiments described above can also be realized in surgical instruments such as integrally-designed endoscope staplers. Moreover, all the embodiments can also be realized in other products such closers and electric scalpels.

According to the surgical instrument of the invention, the flexible components are adopted to realize bending of the actuator relative to the far end of the extension tube so that the actuator can bend by a larger angle to adapt to medical treatment under more complex clinic conditions. For instance, surgery can be performed in parts with limited spaces (such as the thoracic cavity and the pelvic cavity) more conveniently, and thus the problems which cannot be solved by other surgical instruments are solved. The surgical instrument provided with the actuator capable of being by a large angle of the invention can achieve focus excision, tissue dissecting and suturing at various unaccessible positions and thus is beneficial to more patients.

The above description and drawings are provided only for illustrative description. Any quotation about the singular forms of elements in the claims, such as the article 'one', 'certain' or 'said', should not be interpreted as the singular number of the elements. For each specific application, those skilled in the field can describe the structure in difference mode, and all these realization modes should fall within the scope of the invention.

Anyone skilled in the field can manufacture or use the invention based on the description before the embodiments disclosed. Various modifications of these embodiments can be easily obtained by those skilled in the field, and the general principle defined in the description can be applied to other embodiments without deviating from the spirit or scope of the invention. Thus, the invention is not limited to the embodiments given in the description, but should be granted the widest scope in accordance with the principle and novelties disclosed in the claims and the description.

What is claimed is:

1. A surgical instrument, comprising an actuator, an extension tube, a controller and a bend control rod, wherein a near end of the extension tube is connected with the controller and a far end of the extension tube is rotatably connected with the actuator to rotate relative to the far end of the extension tube;

wherein the extension tube includes a first flexible strap and a second flexible strap, a far end of the first flexible strap and a far end of the second flexible being respectively connected to the actuator on two opposing sides of a central axis of the actuator, the first flexible strap and the second flexible strap each having a width that is greater than the thickness, the thickness direction being a direction of rotation of the actuator, wherein the extension tube includes a pair of counter-moving racks including a first rack and a second rack, a near end of the first flexible strap being attached to the first rack and a near end of the second flexible strap being attracted to the second rack, each of the first rack and the second rack being coupled to each other and arranged within the extension tube in a counter moving arrangement such that:

when the first rack moves towards the near end of the extension tube, the first flexible strap is tensioned, the second rack moves towards the far end of the extension tube, and the second flexible strap is released;

when the first rack moves towards the far end of the extension tube, the first flexible strap is released, the second rack moves toward the near end of the extension tube, and the second flexible strap is tensioned, the first flexible strap is released, wherein, when each of the first flexible strap or the second flexible strap are tensioned, the first flexible strap or the second flexible strap generates displacement to rotate the actuator and the displacement generated by the first flexible strap and the displacement generated by the second flexible strap are opposite, wherein the controller is operatively coupled to the bend control rod to linearly translate the bend control rod towards the near end of the extension rod and the far end of the extension rod, the bend control rod being attached to the first rack (i) to pull the first rack towards the near end of the extension rod when the controller linearly translates the bend control rod towards the near end of the extension rod, and (ii) to push the first rack towards the far end of the extension rod when the controller linearly translates the bend control rod towards the far end of the extension rod;

wherein the extension tube further includes a magazine sleeve, a first magazine inner tube and a second magazine inner tube, and the first magazine inner tube and the second magazine inner tube are coaxial with the magazine sleeve; and wherein the instrument further includes two intermediate connectors, a first connecting piece and a second connecting piece, the two intermediate connectors are connected to the actuator, one of the two intermediate connectors is connected to the first magazine inner tube through the second connecting piece, and the other one of the two intermediate connectors is connected to the second magazine inner tube through the first connecting piece.

2. The surgical instrument according to claim 1, the first rack and the second rack being operatively coupled to each other by a gear engaged with the first rack and the second rack.

3. The surgical instrument according to claim 2, wherein the first rack and the second rack are arranged on the two sides of the gear, the bend control rod are arranged in the magazine sleeve, the far end of the bend control rod is fixedly connected with the first rack, the first rack is further fixedly connected with the near end of the first flexible strap, and the second rack is fixedly connected with the near end of the second flexible strap.

4. The surgical instrument according to claim 3, wherein the gear is rotatably arranged on the first magazine inner tube or the second magazine inner tube.

5. The surgical instrument according to claim 1, wherein the actuator includes an anvil assembly and a cartridge assembly, wherein the cartridge assembly comprises a cartridge, one or more suturing staples, one or more staple pushing blocks, and a cartridge holder, wherein the surgical instrument further comprises a driving assembly, and the driving assembly comprises a cutter and a flexible cutter bar, and wherein the near end of the anvil assembly is movably connected with the near end of the cartridge holder, and the driving assembly drives the actuator switch to a first state or a second state.

6. The surgical instrument according to claim 1, wherein: the rotation angle of the actuator towards at least one side relative to the far end of the extension tube is any numerical value from 0° to 180°, wherein the rotation angle is an angle between a central axis of the extension tube and a central axis of the actuator.

7. The surgical instrument according to claim 1, wherein at least one flexible strap of the first flexible strap and the second flexible strap is configured to provide rotation torque for the actuator with the one or more rotary hinges as the rotation axis.

* * * * *